United States Patent

Goodwin et al.

[11] Patent Number: 6,066,776
[45] Date of Patent: May 23, 2000

[54] SELF-FORMING PROSTHESIS FOR REPAIR OF SOFT TISSUE DEFECTS

[75] Inventors: Jonathan L. Goodwin, Nashua; Peter H. Gingras, Windham; Steve A. Herweck, Nashua, all of N.H.

[73] Assignee: Atrium Medical Corporation, Hudson, N.H.

[21] Appl. No.: 08/895,050

[22] Filed: Jul. 16, 1997

[51] Int. Cl.$^7$ .................................................. A61F 2/02
[52] U.S. Cl. .......................... 623/11; 623/901; 606/151; 606/213
[58] Field of Search ..................... 606/151, 153, 606/155, 156, 213–215; 600/37; 623/11, 12, 13

[56] References Cited

U.S. PATENT DOCUMENTS

| | | | |
|---|---|---|---|
| 4,769,038 | 9/1988 | Bendavid et al. | 623/13 |
| 5,116,357 | 5/1992 | Eberbach | 606/151 |
| 5,147,374 | 9/1992 | Fernandez | 606/151 |
| 5,333,624 | 8/1994 | Tovey | 128/897 |
| 5,356,432 | 10/1994 | Rutkow et al. | 623/11 |
| 5,368,602 | 11/1994 | de la Torre | 606/151 |
| 5,456,720 | 10/1995 | Schultz et al. | 623/12 |
| 5,545,178 | 8/1996 | Kensey et al. | 606/213 |
| 5,593,441 | 1/1997 | Lichtenstein et al. | 623/11 |
| 5,634,931 | 6/1997 | Kugel | 606/151 |
| 5,716,408 | 2/1998 | Eldridge et al. | 623/11 |
| 5,743,917 | 4/1998 | Saxon | 623/11 |
| 5,879,366 | 3/1999 | Shaw et al. | 606/213 |
| 5,919,232 | 7/1999 | Chaffringeon et al. | 606/151 |
| 5,922,026 | 7/1999 | Chin | 623/11 |

FOREIGN PATENT DOCUMENTS

WO 93/17635   9/1993   WIPO.
WO 97/21461   6/1997   WIPO.

OTHER PUBLICATIONS

Rutkow and Robbins, "Tension–free" Inguinal Herniorrhaphy: A Preliminary Report on the "Mesh Plug" Technique, *Surgery*, vol. 114, No. 1, (Jul. 1993) pp. 3–8.

Shulman, A.G. et al., "Prosthetic Mesh Plug Repair of Femoral and Recurrent Inguinal hernias: The American Experience", *Annals of the Royal College of Surgeons of England*, (1992) vol. 74, pp. 97–99.

Gilbert, A.I., "Sutureless Repair of Inguinal Hernia", *The American Journal of Surgery*, vol. 163 (Mar. 1992) pp. 331–335.

*Primary Examiner*—Michael J. Milano
*Assistant Examiner*—Tram A. Nguyen
*Attorney, Agent, or Firm*—Lahive & Cockfield, LLP

[57] ABSTRACT

A prosthesis is provided that is advantageously used to fill a soft tissue or muscle defect, such as an inquinal or femoral hernia. In a first aspect of the invention, multiple layers of a flexible, mesh material are attach together at a finite number of joins. A tab is placed at the geometric center of one of the mesh layers to facilitate insertion of the mesh into the defect. The tab also creates a blunt tip that reduces irritation and discomfort to the patient. In a second aspect of the invention, a prosthesis is provided that includes a barrier layer between two or more layers of flexible, mesh material to prevent adhesion of the device to the tissue. All layers are attached together by a finite number of joins. A tab is placed at the geometric center of one of the mesh layers to facilitate insertion of the mesh into the defect. The prostheses of the invention are self-forming in that they change from a two dimensional configuration to a three dimensional configuration upon insertion of the device into the defect.

26 Claims, 2 Drawing Sheets

SELF-FORMING PROSTHESIS FOR REPAIR OF SOFT TISSUE DEFECTS

FIELD OF THE INVENTION

The present invention relates generally to a surgical prosthesis for repair of soft tissue defects, and more particularly to a surgical prosthesis that is composed of surgical mesh and is self-forming to readily adapt to the contour of the defect.

BACKGROUND OF THE INVENTION

The most common operation performed by general surgeons in the United States is inguinal herniorrhaphy. Over 600,000 such procedures are performed annually. Lichtenstein and Shore first began using a plug composed of surgical mesh to treat femoral hernias and recurrent inguinal hernias in 1968. The plug consisted of a roll of surgical mesh that was coiled into a plug and inserted into the defect to fill the defect. The plug concept of treating a hernia developed by Lichtenstein and Shore was shown to be a simpler and more reliable repair than the previous conventional technique of suturing the defect to close. The rate of recurrent herniation proved to be very low compared to the former technique. The plug, however, lacks radial support to maintain its position within the defect.

Later, Gilbert and Rutkow began treating primary and recurrent hernias with an umbrella plug. A swath of surgical mesh was rolled into a cone shape and inserted into the tissue defect to occlude the void. While the plug provides more radial support than the plug of Lichtenstein and Shore, the plug, has certain disadvantages. The plug lacks the needed interior bulk to solidly fill the opening. Furthermore, the apex end of the conical mesh structure is inserted first into the defect, producing a sharp pointed edge which could cause irritation to the underlying tissue and discomfort to the patient. Since the plug is preformed and in a conical shape, it can only fill defects that are approximately its shape.

Fernandez in U.S. Pat. No. 5,147,374 disclosed a prosthetic patch for hernia repair. The patch is fabricated from a rolled up flat sheet of polypropylene or PTFE surgical mesh. The sheet of surgical mesh is rolled into a cylinder and bound together by catgut to hold its shape. One end of the rolled up mesh is cut with multiple slits to form flared out flaps. The flaps are sutured to a second sheet of surgical mesh. The patch is compressed into a cylindrical longitudinal structure and a trocar is used to insert it into the defect. Like the plug of Lichtenstein and Shore, this plug lacks radial support to maintain it in position and thus requires stitching of the covering mesh to the soft tissue to hold its position. The plug is preformed in a circular cross section and consequently does not conform well to variances in the contour of the defect.

The C.R. Bard Co. of Billerica, Mass. has introduced a preformed plug under the tradename PerFix Plug for hernia repair. The plug is cone shaped and fabricated from a layer of surgical mesh that is pleated to contact the contour of the defect. Multiple layers of a fill mesh provide bulk to fill the void. The plug is compressible, but because it is preformed and has a preset shape it does not exert significant outward radial force within the defect to prevent protrusion of material through the defect. While the plug has a more bunt tip at the apex of the cone than the plug of Gilbert and Rutkow, it still has a rather sharp tip that may cause irritation to the underlying tissue and discomfort to the patient.

What is clearly needed is a self-forming prosthesis for hernia repair that anatomically conforms well to the contours of a wide variety of defects, is easily insertable into the defect while having a blunt tip to seal the defect, minimize irritation and reduce discomfort in the patient after insertion.

OBJECTS OF THE INVENTION

It is an object of the invention to obviate the above noted disadvantages of the prior art.

It is a further object of the invention to provide for a self-forming prosthesis that can be advantageously used to repair a soft tissue defect.

It is a further object of the invention to provide for a self-forming prosthesis that can be deformed from a planar configuration to a 3-dimensional structure.

It is a still further object of the invention to provide for a self-forming prosthesis that can be advantageously used to repair a soft tissue defect and that upon insertion anatomically conforms to the contour and size of the defect.

It is a yet further object of the invention to provide for a self-forming prosthesis that naturally exerts an outward radial pressure on the defect to maintain position within the defect.

Other general and more specific objects of the invention will in part be obvious and will in part appear from the drawings and description which follow.

SUMMARY OF THE INVENTION

The invention addresses the need for a prosthesis advantageously suited for repair of a soft tissue or muscle defect.

In one aspect of the invention, a prosthesis is provided that is fabricated from multiple layers of a flat surgical mesh. The mesh layers are cut into a circular shape and placed in alignment on top of each other. In the preferred embodiment, the layers of mesh are attached to each other by a finite number of joins that are radially distributed from the center of the mesh material. A tab of surgical material is attached to one of the layers of the mesh material to allow for easy insertion of the prosthesis into the defect.

In a further aspect of the invention, a second prosthesis is disclosed having a layer of polytetrafluoroethylene or other suitable barrier between two layers of surgical mesh to prevent adhesion formation with the tissue. The two layers of mesh and the one layer of barrier material are attached by a finite number of joins that are preferably radially distributed from the center of the layers. The prosthesis also includes a tab which is attached to one layer of the surgical mesh for easy insertion of the device into the defect.

In a yet further aspect of the invention, a method for repairing a soft tissue or muscle defect is described in which the prostheses of the invention are forcibly urged into the defect while the configuration of the prosthesis changes from a planar structure to a 3-dimensional structure to fill the defect.

BRIEF DESCRIPTION OF THE DRAWINGS

The foregoing and other objects, features and advantages of the invention will be apparent from the following description and from the accompanying drawings, in which like reference characters refer to the same parts throughout the different figures. The drawings illustrate principles of the invention and, are not intended to be to scale.

DETAILED DESCRIPTION OF AN ILLUSTRATIVE EMBODIMENT

Throughout the following detailed description, the same reference numbers refer to the same elements in all figures.

Figure 1:
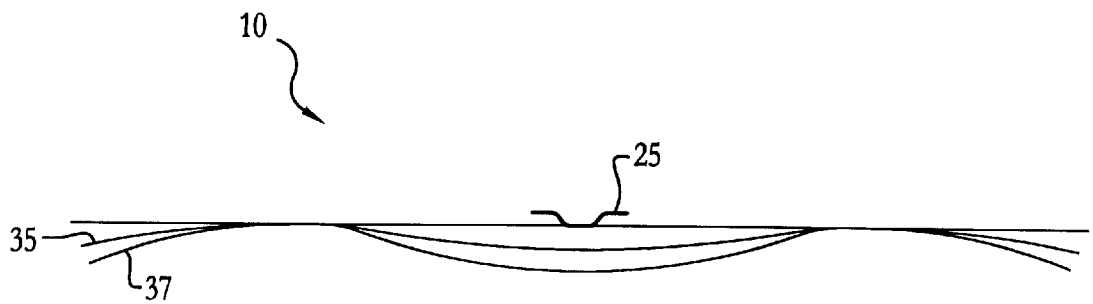
FIG. 1 is a side view of a multi layer prosthesis in accordance with one embodiment of the invention.

FIG. 1 shows a prosthesis 10 in accordance with the present invention that is composed of a layer of flexible surgical mesh 15, cut from a planar sheet of the material. The mesh may be cut using techniques such as laser cutting, hot knives, or shears that are well known to those of ordinary skill in the art. The layer of surgical mesh may be cut in a variety of shapes. The shape of the cut is determined by the intended application of the prosthesis. Shapes intended to be within the scope of the invention include but are not limited to a circular, rectangular, square, or oval geometry. In the preferred embodiment of the invention, the shape of the layer of surgical mesh 15 is circular. Mesh 15 is preferably fabricated from polypropylene. A mesh suitable to practice the present invention is available under the name of Atrium Polypropylene Mesh, which is a product of the Atrium Medical Corporation of Hudson, N.H. While mesh 15 is preferably a polypropylene mesh, other mesh materials such as polytetrafluoroethylene, polyethylene terephthalate, or other biomaterial suitable for surgical applications are contemplated to be within the scope of the invention.

A suitable biomaterial is any biomaterial used for constructing the prosthesis that performs with an appropriate host response for the specific application. In particular, the biomaterial will have sufficient strength and integrity while evoking a mild inflammatory response. The biomaterial can have physical and chemical characteristics that either promote or inhibit tissue ingrowth and attachment to surrounding tissues.

A tab 25 is attached to mesh 15 at the center of the mesh to facilitate mesh implantation, when mesh 15 and tab 25 are deformed into a 3-dimensional structure from a substantially planar structure. Tab 25 is preferably cut from polypropylene mesh, but any flexible surgical material is contemplated to be within the scope of the invention. Tab 25 is attached to mesh 15 by any technique acceptable for the intended surgical application. Examples include but are not limited to ultrasonic welding, vibration welding, heat stamping, suturing, and bonding. Tab 25 is preferably rectangular in shape, but other shapes are not considered precluded from the scope of the invention.

Prosthesis 10 is in the preferred embodiment a multi layered mesh. Prosthesis 10 will now be described in relation to a three layered mesh. However, one of ordinary skill in the art will recognize that the prosthesis of the invention is not limited to only three layers, but encompasses any number of layers, including a prosthesis with only one or two layers. Mesh 15 with attached tab 25 is positioned on top of two layers of planar surgical mesh 35, 37 and aligned with meshes 35, 37. Meshes 35, 37 are preferably polypropylene, but any mesh suitable for surgical applications may be used. Meshes 35, 37 are preferably the same shape as mesh 15, but other shapes are considered within the scope of the invention. Meshes 15, 35, 37 are preferably circular in shape.

Figure 2:
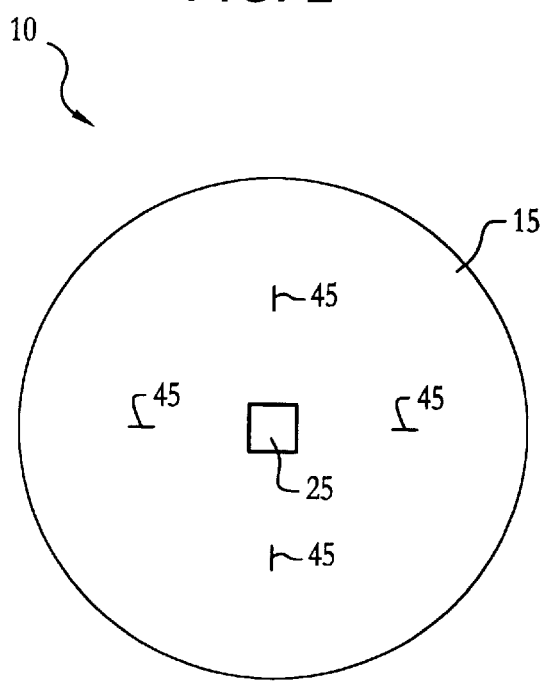
FIG. 2 is a top view of the prosthesis of FIG. 1, in which the tab and joins of the prosthesis are shown.

Mesh 15 is attached to meshes 35, 37 at a finite number of joins 45 as shown in FIG. 2 Joins 45 are preferably created through ultrasonic welding of the three mesh layers 15, 35, and 37 but other attachment techniques compatible with surgical applications are contemplated to be within the scope of the invention. Joins 45 are preferably located radially from the center of the meshes 15 and 35, and spaced apart by 90 degrees, but other patterns may be practiced that one of ordinary skill in the art will recognize that fall within the scope of the invention.

Prosthesis 10, as described above, is comprised of multiple layers of mesh to provide bulk to the device. Each layer of mesh is attached to the other layers of mesh by joins 45. The number of layers of mesh used to form the prosthesis is application dependent, as long as the prosthesis maintains its flexibility to deform from a planar geometry to a 3-dimensional structure.

A first example of a prosthesis fabricated in accordance with the invention includes a sheet of polypropylene mesh that is laser cut into three 3.0" diameter circles and one 0.38"×0.75" rectangle. The 0.38"×0.75" rectangle is centered on top of one 3.0" circle and ultrasonically welded together. The weld is approximately 0.25"×0.13" and is centered on the circle. This welded unit is then placed on top of the two remaining 3.0" circles and aligned. The three layers are ultrasonically welded together. The welds are four 0.25"×0.13" rectangular welds, radiating from the center of the device. The welds are equally spaced 90° apart and are placed 1.0" from the center of the device. In a second example of a prosthesis in according to the invention, a sheet of polypropylene is laser cut into three 3.75" diameter circles. The three circles are aligned and ultrasonically welded together. The weld pattern is a 0.38" square in the center of the device with four lines radiating from each corner of the square to the perimeter of the device. The welds are approximately 0.13" wide. In a third example the sheet of mesh is laser cut into two 2.25" diameter circles. The two circles are aligned and ultrasonically welded in the center with the weld pattern of an "X". Each line of the "X" is approximately 0.13"×0.5". In another example, the mesh is laser cut into two 3.0" diameter circles and one 3.0" diameter circle that has four equally spaced 0.25" square tabs along the perimeter. The three components are aligned with the circle with four tabs on the bottom. The three components are ultrasonically welded together with a weld pattern of four 0.25"×0.13" radial welds at each tab and a 0.38" square in the center.

Figure 3:
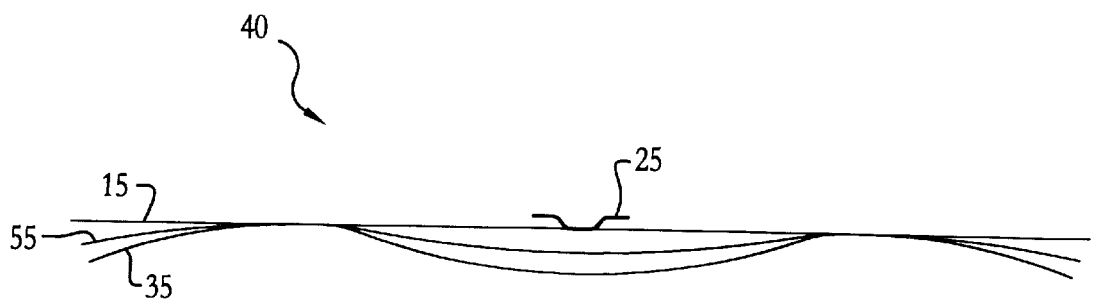
FIG. 3 is an alternate embodiment of a multi layer prosthesis in accordance with the invention.

An alternative embodiment of a prosthesis in accordance with the invention is shown in FIG. 3 that prevents tissue adhesion formation when prosthesis 40 is inserted into the tissue defect. The prosthesis 40 has a first mesh layer 15 preferably composed of polypropylene mesh and a tab 25 that is attached to the geometric center as described above. A sheet of polytetrafluoroethylene is cut to produce a layer 55 of material with similar dimensions as mesh 15, and a second mesh layer of mesh 35 is cut again to similar dimensions as mesh 15. Mesh 15 is placed on top of layer 55 which is placed on top of mesh 35. The three layers 15, 35, and 55 are attached together by joins 45. Again the joins 45 are preferably radially distributed from the center of the aligned meshes 15, 35, and 55, and spaced at 90 degree intervals around the prosthesis.

Figure 4:
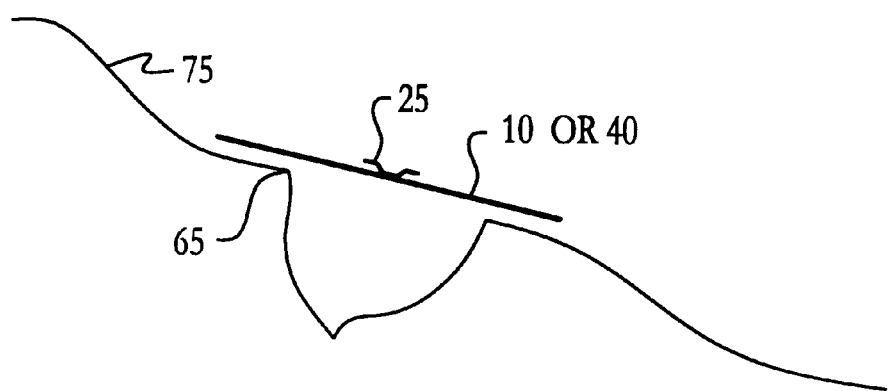
FIG. 4 is a side view of a soft tissue defect and a prosthesis placed over the defect but not yet inserted therein.
Figure 5:
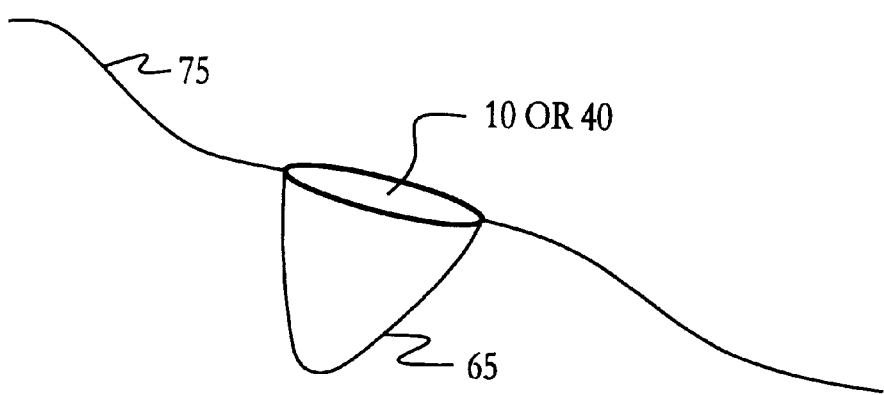
FIG. 5 is a side view of a soft tissue defect with the prosthesis in accordance with the instant invention inserted therein.

The prostheses 10, and 40 of the current invention are advantageously used to repair soft tissue or muscle defects in patients as is shown in FIGS. 4 and 5. Typically these defects consist of an opening or hole 65 that has developed in the wall 75 of an organ, allowing interior organs to protrude through the opening. Femoral and inguinal hernias are common examples of soft tissue defects. To repair the defect, a prosthesis 10, or 40 of the instant invention is placed within the defect 65 to fill the void. Prosthesis 10 or 40 is forcibly urged into the defect 65 using laparotomy methods by grasping, pinching, or pushing tab 25 with a surgical instrument to deform the prosthesis 10 or 40 from a planar configuration to a 3-dimensional structure as shown in FIG. 5. Prosthesis 10 or 40 is consequently said to be self-forming within the defect in changing from a planar configuration to a 3-dimensional structure. The multiple layers of the prosthesis 10 or 40 assume a 3-dimensional shape which anatomically conforms to the size of the defect 65. Since the prosthesis 10 or 40 is self forming within the defect, the prosthesis better adapts to the contour of the wall of the defect as it is being implanted. Furthermore, the prosthesis naturally exerts an outward radial force on the defect to maintain the position of the prosthesis in the defect. Tab 25 allows a physician to grasp the prosthesis easily for a simple insertion into the defect. Prosthesis 10 or 40 when inserted creates a blunt tip which thus may reduce irritation to underlying tissue and any discomfort associated with the device.

It is thus seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is desired to be secured by Letters Patent is:

We claim:

1. A prosthesis for repairing a tissue or muscle wall defect comprising:
   a layer formed of a flexible surgical mesh fabric for tissue ingrowth with a substantially planar tab attached thereto, the center of said tab being attached to the geometric center of said layer, said tab being substantially smaller in area than said layer;
   wherein said layer is self-forming about said tab from a first configuration, which is substantially planar, to a second configuration, which approximates the contour of the defect upon forcibly urging said prosthesis into the defect.

2. The prosthesis of claim 1 wherein said layer is circular in shape.

3. The prosthesis of claim 1 wherein said flexible surgical mesh fabric is selected from the group consisting of polypropylene, polytetrafluoroethylene, and polyethylene terephthalate.

4. The prosthesis of claim 1 wherein said second configuration has a 3-dimensional shape.

5. A prosthesis for repairing a tissue or muscle wall defect comprising:
   a layer formed of a flexible surgical mesh fabric for tissue ingrowth with a substantially planar tab attached thereto, the center of said tab being attached to the geometric center of said layer, said tab being substantially smaller in area than said layer;
   wherein said layer is self-forming about said tab from a first configuration, which is substantially planar, to a second configuration, which occludes the defect upon forcibly urging said tab into the defect.

6. The prosthesis of claim 5 wherein said first layer is circular in shape.

7. The prosthesis of claim 5 wherein said flexible surgical mesh fabric is selected from the group consisting of polypropylene, polytetrafluoroethylene, and polyethylene terephthalate.

8. A prosthesis for repairing a tissue or muscle wall defect comprising:
   a first layer formed of a flexible surgical mesh fabric for tissue ingrowth;
   a second layer formed of a second flexible surgical fabric and attached to said first layer by two or more joins, each of said joins being spaced radially about the geometric center of the first layer and being spaced at a predetermined interval from an adjacent join, at least two of said joins being non-linearly aligned;
   wherein said first and second layer are self-forming from a first configuration, in which said first and second layers are substantially planar, to a second configuration, which approximates the shape of the defect upon forcibly urging said first and second layers into the defect.

9. The prosthesis of claim 8 wherein said first layer is circular in shape.

10. The prosthesis of claim 8 wherein said first layer includes a substantially planar tab at the geometric center for applying force to urge said first and second layers into the defect.

11. The prosthesis of claim 8 wherein said flexible surgical mesh fabric is selected from the group consisting of polypropylene, polytetrafluoroethylene, and polyethylene terephthalate.

12. The prosthesis of claim 8 wherein said second layer is circular in shape.

13. The prosthesis of claim 8 wherein said joins are spaced apart by 90 degrees.

14. A method for repairing a defect in a tissue or muscle wall, comprising the steps of:
   providing a layer formed of a flexible surgical mesh fabric for tissue ingrowth; said layer of flexible surgical mesh fabric including a substantially planar tab attached thereto, the center of said tab being attached to the geometric center of said layer for applying force to urge said layer into the defect, said tab being substantially smaller in area than said layer, said layer being self-forming from a first configuration, which is substantially planar, to a second configuration, which occludes the defect upon forcibly urging said layer into the defect; and
   forcibly urging said layer of flexible surgical mesh fabric into said defect to occlude said defect.

15. The method of claim 14 wherein said layer of flexible surgical mesh fabric is circular in shape.

16. The method of claim 14 wherein said flexible surgical mesh fabric is selected from the group consisting of polypropylene, polytetrafluoroethylene, and polyethylene terephthalate.

17. A method for repairing a defect in a tissue or muscle wall, comprising the steps of:
   providing a flexible first layer formed of surgical mesh fabric for tissue ingrowth attached by two or more joins to a flexible second layer formed of a second surgical fabric, each of said joins being spaced radially about the geometric center of said first layer and being spaced at a predetermined interval from an adjacent join, at least two of said joins being non-linearly aligned;

changing said first and second layers from a first configuration, in which said first and second layers are substantially planar, to a second configuration, which approximates the shape of the defect upon forcibly urging said first and second layers into the defect.

18. A prosthesis for repairing a tissue or muscle wall defect comprising:

a first layer formed of a flexible surgical mesh fabric for tissue ingrowth;

a second layer formed of a second flexible surgical fabric;

a barrier layer positioned between said first and second layers for preventing tissue adhesion;

wherein said first layer, said second layer, and said barrier layer are attached by two or more joins spaced radially about the geometric center of the first layer, each of said joins being spaced at a predetermined interval from an adjacent join, at least two of said joins being non-linearly aligned, and wherein said first layer, said second layer, and said barrier layer are self-forming from a first configuration, in which said first layer, said second layer, and said barrier layer are substantially planar, to a second configuration, which approximates the shape of the defect upon forcibly urging said first, second, and barrier layers into the defect.

19. The prosthesis of claim 18 wherein said first layer is circular in shape.

20. The prosthesis of claim 18 wherein said first layer includes a substantially planar tab at the geometric center for applying force to urge said first and second layers into the defect.

21. The prosthesis of claim 18 wherein said first flexible surgical mesh fabric is selected from the group consisting of polypropylene, polytetrafluoroethylene, and polyethylene terephthalate.

22. The prosthesis of claim 18 wherein said second layer is circular in shape.

23. The prosthesis of claim 18 wherein said joins are spaced apart by 90 degrees.

24. A method of manufacturing a prosthesis for repairing a defect in a tissue or muscle wall comprising the steps of:

providing a first sheet of biomaterial, forming a substantially planar tab of biomaterial for facilitating insertion of the prosthesis into the tissue defect, the tab being substantially smaller in area than the first sheet of biomaterial, and joining the center of the substantially planar tab to the geometric center of the first sheet of biomaterial, wherein the first sheet of biomaterial is self-forming about the tab from a first configuration, which is substantially planar, to a second configuration, which approximates the contour of the defect upon forcibly urging the prosthesis into the defect.

25. The method of claim 24, further comprising the steps of providing a second sheet of biomaterial, and attaching the first sheet of biomaterial to the second sheet of biomaterial at a fixed number of joins spaced radial at predetermined intervals about the geometric center of the first sheet.

26. A method of manufacturing a prosthesis for repairing a defect in a tissue or muscle wall comprising the steps of:

providing a first sheet of biomaterial, providing a second sheet of biomaterial, attaching the first sheet of biomaterial to the second sheet of biomaterial by two or more joins spaced radially about the geometric center of the first sheet and spacing each of said joins at a predetermined interval from an adjacent join, at least two of said joins being non-linearly aligned, wherein the first and second sheets of biomaterial are self-forming from a first configuration, in which said first and second sheets are substantially planar, to a second configuration, which approximates the contour of the defect upon forcibly urging the prosthesis into the defect.

* * * * *

UNITED STATES PATENT AND TRADEMARK OFFICE
CERTIFICATE OF CORRECTION

PATENT NO. : 6,066,776
DATED : May 23, 2000
INVENTOR(S) : Jonathan L. Goodwin, Peter H. Gingras, and Steve A. Herweck Page 1 of 1

It is certified that error appears in the above-identified patent and that said Letters Patent is hereby corrected as shown below:

Column 4,
Line 33, please replace "...from each corner of the..." with -- "...from each corner of the..." --

Column 5,
Line 34, please replace "...what is desired to be..." with -- "... what is claimed as new and desired to be..." --

Signed and Sealed this

Eighth Day of January, 2002

Attest:

JAMES E. ROGAN
Attesting Officer    Director of the United States Patent and Trademark Office